United States Patent [19]
Williams et al.

[11] Patent Number: 5,679,344
[45] Date of Patent: Oct. 21, 1997

[54] GLUCOSAMINE COMPOSITION AND METHOD

[75] Inventors: Susan K. Williams, 4D, 3701 Turtle Creek Blvd., Dallas, Tex. 75219; Stanley A. Bynum, Mesa, Ariz.

[73] Assignee: Susan K. Williams, Dallas, Tex.

[21] Appl. No.: 504,714

[22] Filed: Jul. 20, 1995

[51] Int. Cl.$^6$ .................... A61K 38/48; A61K 31/70; A61K 38/54; A61K 38/47

[52] U.S. Cl. ................ 424/94.63; 424/94.2; 424/94.6; 424/94.61; 424/94.64; 424/451; 424/464; 514/825

[58] Field of Search .................... 424/439, 451, 424/464, 94.2, 94.6, 94.61, 94.64; 514/825

[56] References Cited

U.S. PATENT DOCUMENTS

| | | | |
|---|---|---|---|
| 3,683,076 | 8/1972 | Rovati | 424/180 |
| 4,647,453 | 3/1987 | Mesner | 514/825 |
| 5,358,720 | 10/1994 | Koppel et al. | 514/825 |
| 5,409,699 | 4/1995 | Kohnert et al. | 424/94.64 |

OTHER PUBLICATIONS

The Merck Index, 11th, Ed., pp. 1491–1492, 1989.
Tarayre et al, Arzneimittel–Forschung (Drug Research) 27 (1): 1144–49 (1977).
Current Medical Research and Opinion, Pujalte et al, vol. 7, No. 2, 1980.
Clinical Therapeutics vol. 3, No. 5, 1981, Vajaradul Medical Hypotheses (1994) 42, 323–327, McCarty.

*Primary Examiner*—Edward J. Webman
*Attorney, Agent, or Firm*—John L. Sigalos

[57] ABSTRACT

A glucosamine-containing composition that includes an anti-inflammatory proteolytic enzyme composition to increase the rapidity of physiological availability of the glucosamine and the method of increasing such availability by the use of proteolytic enzymes.

14 Claims, No Drawings

GLUCOSAMINE COMPOSITION AND METHOD

BACKGROUND OF THE INVENTION

The instant invention relates to glucosamine compositions capable of exerting a more rapid beneficial effect of the glucosamine and to the method of increasing the effectiveness of such compositions.

Glucosamine is an amino sugar known to normalize cartilage metabolism, inhibit degradation, and stimulate the synthesis of proteoglycans. The proteoglycans are important constituents of articular cartilage. Thus, glucosamine is given to assist in the healing of joint and connective disease damage.

Although known to have this function for many years and to be administered for certain types of injuries and degenerative conditions where there has been damage to articular cartilage discs and connective tissue, it has been found that it takes an extended period of time after administration before it can exercise its beneficial effect. For reasons not clearly understood, it is difficult to get an immediate response on the administration of glucosamine and, accordingly, it may be a period of several months before any physiologically beneficial effect can be realized.

Thus, while compositions are available which utilize glucosamines for treatment of articular disorders, it is found that they are not immediately effective and in some instances must be given for periods of months before they can exercise their desired effect.

SUMMARY OF THE INVENTION

While not completely understood, it is believed that the very slow-acting effect of existing glucosamine compositions is due to the fact they are given in forms that are not readily utilizable to form proteoglycans and that the inflammatory conditions associated with articular damage may complicate the bodies' ability to rapidly utilize the same.

The present invention overcomes the problems of prior glucosamine preparations and results in compositions that enable a more rapid uptake of glucosamine, permitting the healing effects of glucosamine to occur.

Briefly stated, the present invention comprises a composition with physiologically effective amounts of a glucosamine and an anti-inflammatory proteolytic composition.

The invention also comprises a method of increasing the rapidity of physiological availability of a physiologically active glucosamine by utilizing therewith an anti-inflammatory proteolytic composition.

DETAILED DESCRIPTION

The two essential components of the instant composition are a physiologically active glucosamine in conjunction with the anti-inflammatory proteolytic composition.

As used herein, the term "physiologically active glucosamine" means any glucosamine which can be utilized by the body. Glucosamine per se and glucosamine salts such as glucosamine sulfate and glucosamine hydrochloride are suitable examples with glucosamine hydrochloride being especially preferred in the instant invention.

As used herein, the term "anti-inflammatory proteolytic enzyme composition" means a combination of at least one protease and at least one acid-stabilized protease. While it is known that proteolytic enzymes possesses anti-inflammatory properties, it has been found that a combination of acid-stabilized proteases and unstabilized proteases is most effective. The proteases are preferably broad spectrum proteases prepared, as is conventionally known, from various strains of *Aspergillus Oryzae*. The preferred protease is trypsin, with pepsin, and other proteases utilizable therewith. Such proteases and acid-stabilized proteases are commercially available under the marks NUTRASE® and NUTRASE®PB18.

As to proportions, the glucosamine and proteolytic enzymes are each added in amounts effective to exert their beneficial effect, i.e., a pharmacologically effective amount. In the case of glucosamine an amount effective for assisting the body in the repair of articular damage, i.e., damage to connective tissues, including articular cartilage and discs due to traumatic and degenerative problems. In the case of the anti-inflammatory proteolytic enzyme composition an amount effective to assist the body in reducing inflammation. While it has been found that about 1,500 milligrams per day of glucosamine is a suitable dose for repair of articular damage, the amount can vary widely dependent mainly on such factors as weight, age, sex, severity of injury, and like factors always considered in prescribing optimum dosages. The amount of the proteolytic enzyme composition can also vary widely based on these same factors and also upon the titer. Thus, for example, for acid stabilized proteases at 750 U and proteases at 1750 HUT an equal blend thereof can be given in an amount of about 10 to 20 parts by weight for each 100 parts by weight of the glucosamine.

It has also been found that the more rapid physiological availability; i.e., more rapid availability of the glucosamine by the body can be assisted by including an amylase and a lipase with the proteolytic enzymes. Any commercially available amylase can be utilized and the same is true with respect to the lipase. As is known, the amylases are enzymes which convert starch into sugars and the lipases are a class of enzymes that hydrolyze fats to glycerol and fatty acids. A particular blend of the protease, amylase and lipase enzymes is available commercially under the mark "NUTRASE"®PB-18.

With respect to the amylase and lipase utilized, they are each present in minor amounts, preferably in more than about 1 to 2.5 parts by weight for each 100 parts by weight of the glucosamine.

It is found for best repair of the articular disorders to include manganese in the composition, manganese being known to be essential for normal skeleton connective tissue development. As in the case with many metals utilized in biological preparations, it is preferred to use it in the form of a chelate. Any commercially available magnesium chelate can be utilized, a preferred one being amino acid chelated manganese sold under the mark "CHELAZOME"® The manganese is utilized in the amount of about 2 to 15 parts by weight, for each 100 parts by weight of the glucosamine.

Also preferably included is a source of ascorbic acid, preferably calcium ascorbate, for its usual effect. Ascorbic acid aids in tissue healing and the calcium form is used to ensure there is no loss thereof from the body due to the adverse effects on calcium by proteolytic enzymes. It is used in amounts of about 10 to 20 parts by weight for each 100 parts by weight of glucosamine. It is evident that calcium or any suitably active calcium compound and ascorbic acid or other suitably active ascorbate can be separately added to the composition.

Other materials conventionally used in pharmaceutical products such as inert fillers can be utilized with the instant composition to form tablets and capsules and to give the composition the desired level of glucosamine.

While not completely understood, it is believed that the utilization of the proteolytic enzymes with the glucosamine makes the glucosamine more readily absorbed and utilized by the body due to the proteolytic enzyme effect on reducing inflammatory conditions. As a consequence, with the adverse effects of inflammation being ameliorated, the body is able to immediately utilize the glucosamine for the repair of the articular damage, rather than having to have, as at present, a one-month or more buildup period before it can start exercising its beneficial effects.

The invention will be further described in connection with the following example which is set forth for purposes of illustration only.

EXAMPLE

A composition was formed by admixing 15,000 parts by weight of glucosamine hydrochloride, 2,350 parts by weight of a proteolytic enzyme blend of "NUTRASE"® and "NUTRASE"® PB-18, 2,000 parts by weight of calcium ascorbate and 1,250 parts of manganese chelate (CHELAZOME®).

After being thoroughly admixed in dry form, the dry pulverulent material was formed into capsules containing 375 milligrams of glucosamine hydrochloride, 750 U of acid stabilized protease, 1750 HUT of protease, 250 DU of amylase, 4 LU of lipase, 50 mg. of calcium ascorbate, and 31.25 mg. of the manganese chelate.

At the present time it is also believed that it is beneficial to include a kinase in the composition, because such can assist in accelerating the anti-inflammatory effect of the proteolytic enzymes.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A nutrient composition for use in articular disorders consisting essentially of pharmacologically effective amounts of a glucosamine and of an anti-inflammatory proteolytic enzyme composition.

2. A nutrient composition for use in articular disorders comprising pharmacologically effective amounts of a glucosamine, an anti-inflammatory proteolytic enzyme composition, at least one amylase and at least one lipase.

3. The nutrient composition of claim 2 also containing chelated manganese.

4. The nutrient composition of claim 3 also containing a source of ascorbic acid.

5. The nutrient composition of claim 4 wherein the glucosamine is glucosamine hydrochloride, the anti-inflammatory proteolytic enzyme composition comprises unstabilized and acid-stabilized proteases, the chelated manganese is an amino acid chelated manganese, and the source of ascorbic acid is calcium ascorbate.

6. The composition of claim 5 wherein for each 100 parts by weight of glucosamine hydrochloride there is 10 to 20 parts by weight of said anti-inflammatory proteolytic enzyme composition, 2 to 15 parts by weight of said chelated manganese, and 10 to 20 parts by weight of calcium ascorbate.

7. A nutrient composition for use in articular disorders consisting essentially of pharmacologically effective amounts of a glucosamine salt, an anti-inflammatory proteolytic enzyme composition consisting of a blend of proteases and acid-stabilized proteases, at least one amylase, at least one lipase, a chelated manganese, and calcium ascorbate.

8. The method of increasing the rapidity of physiological availability of a pharmacologically active glucosamine comprising admixing therewith a composition consisting essentially of an anti-inflammatory proteolytic enzyme in an amount effective to exert an anti-inflammatory effect.

9. The method of increasing the rapidity of physiological availability of a pharmacologically active glucosamine comprising admixing therewith an anti-inflammatory proteolytic enzyme in an amount effective to exert an anti-inflammatory effect, at least one amylase and at least one lipase.

10. The method of claim 9 wherein a chelated manganese is also admixed with said glucosamine.

11. The method of claim 10 wherein a source of ascorbic acid is also admixed with said glucosamine.

12. The method of claim 11 wherein the glucosamine is glucosamine hydrochloride, the anti-inflammatory proteolytic enzyme composition comprises unstabilized and acid-stabilized proteases, the chelated manganese is an amino acid chelated manganese, and the source of ascorbic acid is calcium ascorbate.

13. The method of claim 12 wherein for each 100 parts by weight of glucosamine hydrochloride there is 10 to 20 parts by weight of said anti-inflammatory proteolytic enzyme composition, 2 to 15 parts by weight of said chelated manganese, and 10 to 20 parts by weight of calcium ascorbate.

14. The method of claim 13 wherein the composition also contains 1 to 2.5 parts by weight of each of an amylase and a lipase for each 100 parts by weight of glucosamine hydrochloride.

* * * * *